(12) United States Patent
Tippett

(10) Patent No.: US 8,128,639 B2
(45) Date of Patent: Mar. 6, 2012

(54) TOOLS AND METHODS FOR HARVESTING FOLLICULAR UNITS

(75) Inventor: Brian E Tippett, Morgan Hill, CA (US)

(73) Assignee: Restoration Robotics, Inc., Mountain View, CA (US)

( * ) Notice: Subject to any disclaimer, the term of this patent is extended or adjusted under 35 U.S.C. 154(b) by 149 days.

(21) Appl. No.: 12/783,750

(22) Filed: May 20, 2010

(65) Prior Publication Data

US 2011/0288562 A1   Nov. 24, 2011

(51) Int. Cl.
*A61B 17/50* (2006.01)

(52) U.S. Cl. ......... 606/133; 606/167; 606/184; 600/562

(58) Field of Classification Search .................. 606/133, 606/184–187; 600/564–568
See application file for complete search history.

(56) References Cited

U.S. PATENT DOCUMENTS

| | | | |
|---|---|---|---|
| 3,605,721 A | 9/1971 | Hallac |
| 3,998,230 A | 12/1976 | Miller |
| 4,160,453 A | 7/1979 | Miller |
| 4,708,147 A | 11/1987 | Haaga |
| 4,716,901 A | 1/1988 | Jackson et al. |
| 4,785,826 A | 11/1988 | Ward |
| 5,036,860 A | 8/1991 | Leigh et al. |
| 5,423,330 A | 6/1995 | Lee |
| 5,480,388 A | 1/1996 | Zadini et al. |
| 5,573,008 A | 11/1996 | Robinson et al. |
| 5,651,781 A | 7/1997 | Grace |
| 5,788,651 A | 8/1998 | Weilandt |
| 5,817,120 A | 10/1998 | Rassman |
| 5,885,226 A | 3/1999 | Rubinstein et al. |
| 5,910,121 A | 6/1999 | Paolo et al. |
| 6,015,391 A | 1/2000 | Rishton et al. |
| 6,080,175 A | 6/2000 | Hogendijk |
| 6,086,543 A | 7/2000 | Anderson et al. |
| 6,110,127 A | 8/2000 | Suzuki |
| 6,142,955 A | 11/2000 | Farascioni et al. |
| 6,273,861 B1 | 8/2001 | Bates et al. |
| 6,306,142 B1 | 10/2001 | Johanson et al. |
| 6,395,002 B1 | 5/2002 | Ellman et al. |
| 6,461,369 B1 | 10/2002 | Kim |

(Continued)

FOREIGN PATENT DOCUMENTS

EP    0966920    12/1999

(Continued)

OTHER PUBLICATIONS

Office Action dated Oct. 25, 2011, in relation to commonly assigned U.S. Appl. No. 12/050,917 (13 pages).

(Continued)

*Primary Examiner* — Tuan Nguyen
(74) *Attorney, Agent, or Firm* — Lena I. Vinitskaya; Sharon Upham

(57) ABSTRACT

Tools and methods are provided for removing biological units from a body surface utilizing a removal tool. The tool is of a concentric tube configuration comprising first and second elongated bodies, in which the second elongated body can be retracted into the first elongated body. The tool may incorporate retention members and mechanisms configured to impede movement of the biological unit in the direction of a distal end of the tool and to improve retention of the biological unit in the tool. Distal fluid or gas delivery may supplement a vacuum in a luminal space to help extract biological units from surrounding tissue.

14 Claims, 2 Drawing Sheets

U.S. PATENT DOCUMENTS

| | | |
|---|---|---|
| 6,471,709 B1 | 10/2002 | Fawzi et al. |
| 6,488,636 B2 | 12/2002 | Bryan et al. |
| 6,554,779 B2 | 4/2003 | Viola et al. |
| 6,875,220 B2 | 4/2005 | Du et al. |
| 6,939,318 B2 | 9/2005 | Stenzel |
| 7,261,721 B2 | 8/2007 | Feller |
| 7,621,933 B2 | 11/2009 | Bodduluri et al. |
| 7,621,934 B2 | 11/2009 | Bodduluri et al. |
| 2002/0151821 A1 | 10/2002 | Castellacci |
| 2003/0097079 A1 | 5/2003 | Garcia |
| 2004/0220589 A1 | 11/2004 | Feller |
| 2005/0085838 A1 | 4/2005 | Thompson et al. |
| 2005/0267506 A1 | 12/2005 | Harris |
| 2006/0161179 A1* | 7/2006 | Kachenmeister ............ 606/133 |
| 2006/0178678 A1* | 8/2006 | Cole ............................ 606/133 |
| 2007/0123800 A1 | 5/2007 | Nishtala et al. |
| 2007/0142743 A1 | 6/2007 | Provencher et al. |
| 2007/0149985 A1 | 6/2007 | Cole |
| 2007/0213634 A1 | 9/2007 | Teague |
| 2007/0213741 A1 | 9/2007 | Cole |
| 2008/0033455 A1 | 2/2008 | Rassman et al. |
| 2008/0045858 A1 | 2/2008 | Tessitore et al. |
| 2008/0154150 A1 | 6/2008 | Goldenberg |
| 2008/0154296 A1 | 6/2008 | Taylor et al. |
| 2008/0234699 A1 | 9/2008 | Oostman et al. |
| 2009/0227895 A1 | 9/2009 | Goldenberg |
| 2009/0240261 A1 | 9/2009 | Drews et al. |

FOREIGN PATENT DOCUMENTS

| | | |
|---|---|---|
| EP | 1293167 | 3/2003 |
| WO | 0207602 | 1/2002 |
| WO | 02065919 | 8/2002 |
| WO | 2005/109799 | 11/2005 |
| WO | 2008027829 | 3/2008 |
| WO | 2009017445 | 2/2009 |

OTHER PUBLICATIONS

Response filed Jul. 27, 2011 to Office Action dated Mar. 28, 2011, in relation to commonly assigned U.S. Appl. No. 12/050,917 (10 pages).

Office Action dated Mar. 28, 2011, in relation to commonly assigned U.S. Appl. No. 12/050,917 (19 pages).

Harris, James A. "New Methodology and Instrumentation for Follicular Unit Extraction: Lower Follicle Transection Rates and Expanded Patient Candidacy", Department of Otolaryngology/Head and Neck Surgery, Univ. of Colorado Health Sciences Center, Denver, Colorado. Copyright 2006 by the American Society of Dermatologic Surgery, Inc. Published by BC Decker, Inc., Dermatologic Surgery, vol. 32.

Robert M Bernstein, MD; William R Rassman, MD. "New Instrumentation for Three-Step Follicular Unit Extraction". Hair Transplant Forum International, vol. 16, No. 1, Jan./Feb. 2006.

* cited by examiner

TOOLS AND METHODS FOR HARVESTING FOLLICULAR UNITS

FIELD OF THE INVENTION

The present application relates generally to tools used for the harvesting of various biological tissue samples, including hair follicles.

BACKGROUND OF THE INVENTION

There are various known tools and instruments for removing biological tissue samples from the body. For example, biopsy needles and punches are used when a small tissue specimen is required for examination, for example, to identify certain medical conditions. Another example of the biological tissue which is often desired to be removed or harvested is a hair follicle. Hair transplantation procedures are well-known, and typically involve harvesting donor hair grafts from the "donor areas," for example, side and back fringe areas of the patient's scalp, and implanting them in a bald area ("recipient area"). Historically, the harvested hair grafts were relatively large (3-5 mm), although more recently the donor grafts may be single "follicular units," which are naturally occurring aggregates of 1-3 (and much less commonly, 4-5) closely spaced hair follicles that are distributed randomly over the surface of the scalp. In one well-known process, a linear portion of the scalp is removed from a donor area by dissection, using a scalpel to cut down to the fatty subcutaneous tissue. The strip is then dissected (under a microscope) into the component follicular units, which are then implanted into a recipient area in respective puncture incisions made by a needle or razor blade. Forceps are typically used to grasp and place the follicular unit grafts into the needle puncture locations, although other instruments and methods are known for doing so.

In another process, singular follicular units are harvested utilizing a hollow needle punch having a cutting edge and an interior lumen with a diameter, for example, of 1 mm. The needle punch is axially aligned with an axis of a follicular unit to be extracted and then advanced into the scalp to cut the scalp about the circumference of the selected follicular unit. Thereafter, the follicular units are removed, e.g., using forceps, for subsequent implantation into a recipient site with a specially devised insertion needle.

SUMMARY OF THE INVENTION

The present application discloses biological tissue removal tools and methods that may be applied to a scalp, skin or other body surface area during various medical, cosmetic, or dermatological procedures. Such devices are especially useful, for example, when harvesting hair follicles or follicular units (FUs). According to an embodiment of the present invention, a biological unit removal tool is provided, configured to minimize damage to the biological unit as it is being removed, to improve the quality and preserve the integrity of the removed specimen. This tool can be utilized manually or in conjunction with a motor powered instrument, or otherwise automated instrument. The tool can be pushed into a body surface, can optionally be rotated, and maneuvered to encapsulate and remove biological units from the body surface accordingly.

According to another embodiment of the invention, there is provided a biological tissue removal tool comprising a first elongated body having a lumen configured to receive a biological unit, and a second elongated body coaxially disposed with respect to the first elongated body and having a sharp distal tip configured to penetrate a body surface. At least one of the first or second elongated bodies is linearly translatable relative to the other. The removal tool is configured such that when the sharp distal tip of the second elongated body is disposed within the first elongated body, the sharp distal tip of the second elongated body is not disposed inside the lumen of the first elongated body. The first elongated body may comprise at least two walls, and the second elongated body may be disposed between the at least two walls of the first elongated body. At least one of the first elongated body or the second elongated body may comprise an internal or external taper. The tool may further include a retention member configured, when in use, to contact the biological unit and impede its movement within the tool in a distal direction. The tool may be configured for connection to a source of reduced pressure to create a pressure differential within the lumen and assist movement of the biological unit in the first elongated body in a proximal direction. In some embodiments, the tool may be a hair harvesting tool. The tool also may be configured to be connected to a robotic arm, and it may be used, for example, in robotic hair transplantation procedures.

According to yet another embodiment of the present invention, there is provided a biological tissue removal tool, comprising a first elongated body having a lumen configured to receive a biological unit, an inner wall defining the lumen and an outer wall; and a second elongated body having a sharp distal tip configured to penetrate a body surface. The second elongated body is disposed between the inner and outer walls of the first elongated body and movable relative to the first elongated body along an axis of the first elongated body to extend out distally or to retract back into a position between the inner and the outer walls of the first elongated body the sharp distal tip of the second elongated body.

According to a further embodiment of the invention, there is provided a biological tissue removal tool, such as a follicular unit removal tool, comprising a first elongated body with a lumen configured to encapsulate the follicular unit, and a second elongated body coaxially disposed with respect to the first elongated body and having a sharp distal tip configured to penetrate a body surface. During at least the withdrawal of the removal tool from the body surface, the sharp distal tip of the second elongated body is either proximal or flush with a distal tip of the first elongated body, so that the encapsulated follicular unit is shielded from the sharp distal tip of the second elongated body by the first elongated body.

Features of the removal tool described in reference to one embodiment may be combined with one or more features described in reference to one or more of the other embodiments.

Also, methods for removing biological tissue from a body surface are provided. One embodiment of such method comprises placing a removal tool adjacent the body surface, the removal tool having a first and a second elongated body, and configured to encapsulate a biological tissue. The method also comprises advancing the second elongated body having a sharp distal tip to penetrate the body surface; and advancing the first elongated body into the body surface such that a distal tip of the first elongated body extends past the sharp distal tip of the second elongated body, and encapsulates biological tissue within a lumen of the first elongated body. In some embodiments, advancing the second elongated body comprises axially moving the second elongated body between an inner and an outer walls of the first elongated body and extending the sharp distal tip of the second elongated body out from between the inner and the outer walls of the first elongated body. The method further comprises withdrawing the removal tool such that the encapsulated biological unit is not exposed to the sharp distal tip of the second elongated body. For example, withdrawing the removal tool may comprise withdrawing the second elongated body such that the second elongated body is not in the lumen of the first elongated body. Furthermore, withdrawing the removal tool may comprise keeping the sharp distal tip of the second elongated body between an inner wall and an outer wall of the first elongated body.

The method may further comprise removing the biological unit from the body surface with assistance of a retention member. The method may further comprise rotating at least one of the first or the second elongated bodies while it is advanced into the body surface. The method may further comprise supplying a fluid or gas under pressure to the distal end of the removal tool.

Other and further objects and advantages of the invention will become apparent from the following detailed description when read in view of the accompanying figures.

BRIEF DESCRIPTION OF THE DRAWINGS

It should be noted that the drawings are not to scale and are intended only as an aid in conjunction with the explanations in the following detailed description. Features and advantages of the present invention will become appreciated as the same become better understood with reference to the specification, claims, and appended drawings wherein:

FIG. 1b show a cross-sectional view along A-A of the tissue removal tool of FIG. 1a.

DETAILED DESCRIPTION OF THE PREFERRED EMBODIMENTS

Figure 1A:
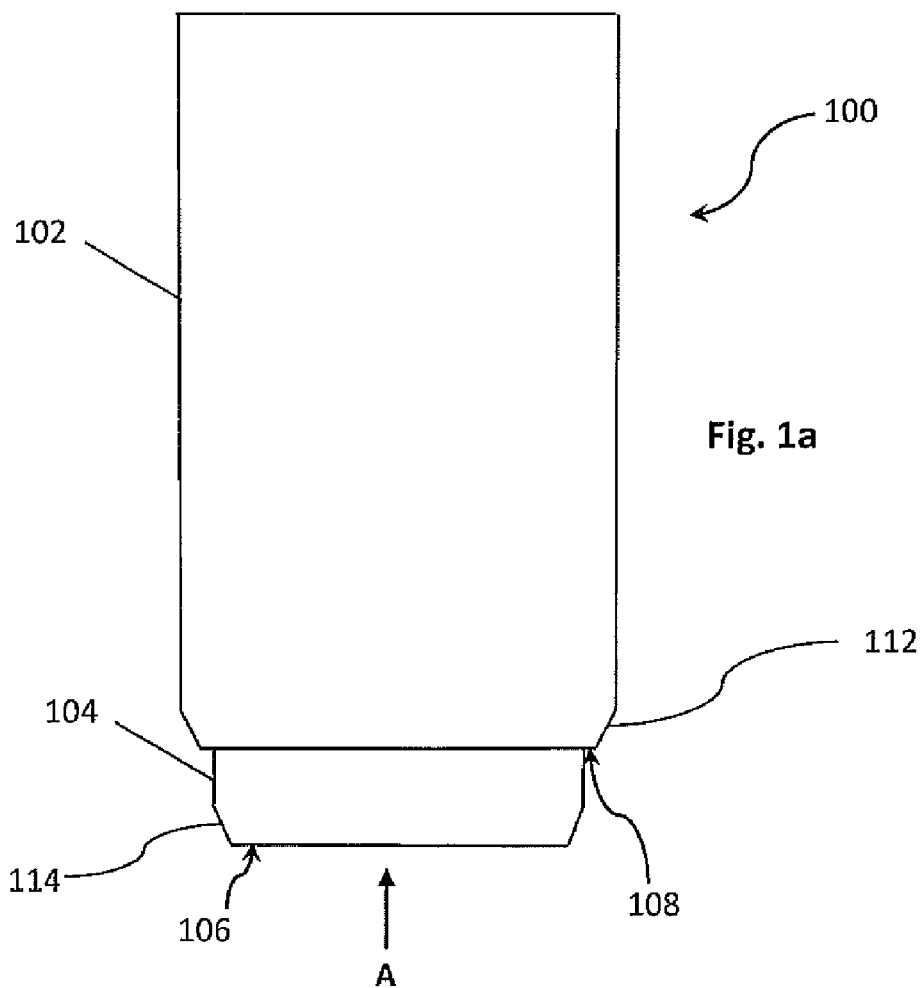
FIG. 1a is a schematic representation of a tissue removal tool in perspective view according to an embodiment of the present invention.

In the following Detailed Description, reference is made to the accompanying drawings that show by way of illustration some exemplary embodiments in which the invention may be practiced. In this regard, directional terminology, such as "distal" and "proximal" etc., is used with reference to the orientation of the Figure(s) being described. Because components or embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following description, therefore, is not to be taken in a limiting sense, and the scope of the present invention is defined by the appended claims.

The various embodiments of the devices and methods of the present application are useful in manual procedures and systems, as well as in automated procedures and systems. The automated systems may also be robotically-assisted or computer/software/machine-instruction controlled. The tools of the current application can also be used with the robotically-assisted systems and procedures and they could be configured for use with those robotic systems, for example, as described in the commonly-assigned US Patent Publication No. 2007/0106306, the disclosure of which is incorporated herein by reference.

The term "tool," or "harvesting or removal tool," or "biological tissue removal tool" as used herein refers to any number of tools or end effectors that are capable of removing or harvesting various biological tissues, for example, follicular units ("FUs") from a body surface. While the removal tools described in the present application are very useful in harvesting follicular units, in general, however, the tools of the present invention may be useful for removing biological units or tissue other than FUs from a body surface. In this sense, a body surface can be attached to the body or may be a flap of skin or body tissue removed from the body. Such tools may have many different forms and configurations. In many embodiments, the tool comprises a hollow tubular shaft and thus may be labeled, for example, a cannula, a needle, or a punch. The distal end of removal tools (for example, punches, coring devices, cutting and/or trimming devices, needles), are typically sharpened, to cut and extract the tissue (e.g., hair follicle).

Various embodiments of follicular unit harvesting cannulas (or tools) described herein may be employed in harvesting systems, whether such systems are fully-automated (e.g., robotically controlled), semi-automated, or manually controlled. It will be appreciated by those skilled in the art that each harvesting cannula design may have certain benefits (e.g., superior retraction and retention of follicular units, less trauma to the surrounding skin and tissue), or drawbacks (e.g., complex design and/or operation, higher manufacturing costs, increased trauma), relative to the other embodiments. Thus, selection of a particular harvesting cannula distal end design will depend on the particular performance criteria sought to be achieved.

"Biological units" or "biological tissue" include discrete units of soft tissue used in cosmetic, diagnostic, and dermatological procedures, for example, various soft tissues, including that extracted for biopsies or grafting. Examples of the biological units particularly useful with the present invention are hair grafts, or follicles, or "follicular unit(s)." Other biological units may be soft tissue used for diagnosis of cancer, such as from the areas of the skin, breast, liver, prostate, colon and small bowel, or lungs. As mentioned above, the term biological units encompasses a number of things, though the present invention is particularly useful in hair harvesting, to provide devices and methods for harvesting follicular units (FUs). As such, the term follicular units (or FUs) will be used herein simply as an example for purposes of describing some embodiments of the present invention with the understanding that it represents more broadly biological units.

According to an embodiment of the present invention, a biological unit removal tool is configured to minimize damage to the biological unit being removed and to improve the quality of the removed specimen, preferably preserving its integrity. This tool can be utilized manually, in conjunction with a motor powered instrument, as part of an automated or semi-automated system, and/or be computer or robotically controlled. The tool may be inserted into a skin, for example, by pushing into a body surface, or optionally it may be rotated, and maneuvered to encapsulate and remove biological units from the body surface accordingly.

FIG. 1a shows a perspective view of one example of such a tissue removal tool. The removal tool 100 includes a first elongated body 102 and a second elongated body 104, which may be substantially coaxially disposed relative to each other. The second elongated body 104 comprises a sharp distal tip 106. The term "sharp" distal tip 106 as used herein means that it is sharp enough to pierce or cut a skin or body surface (not shown). The second elongated body may be pushed into the skin such that its sharp distal tip cuts or incises tissue, or skin layers to a desired depth (e.g. through the epidermis, or upper dermis). The first elongated body 102 comprises a distal tip 108, which is preferably blunt. The blunt distal tip 108 of the first elongated body 102 is less sharp than the distal tip 106. However, the blunt distal tip 108 is capable of readily advancing through the incision created by the sharp distal tip 106 of the second elongated body 104, and continue advancing deeper through the tissue that surrounds a biological unit, such as a follicular unit, without causing any unnecessary damage and/or trauma to the biological unit, and preferably enabling removal of the biological unit while preserving its integrity. The elongated body 102 is configured to at least partially surround or encapsulate the biological unit, with the lumen 110 configured to receive the biological unit (not shown). One or both of the first and second elongated bodies, 102 and 104 respectively, may be axially movable relative to one another, and optionally radially movable relative to one another.

Figure 1B:
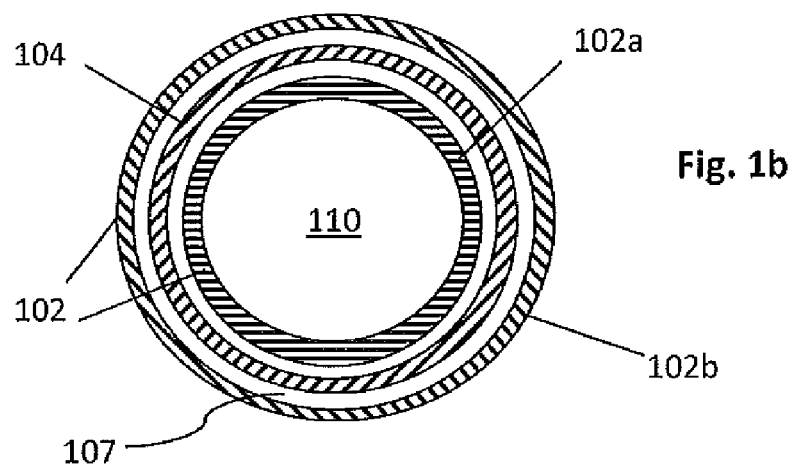

FIG. 1b shows an example of an end view of the removal tool 100, viewed from the direction of arrow A in FIG. 1a. In this particular configuration, the first elongated body 102 comprises a first member or an inner wall 102a and a second member or an outer wall 102b, which together form a structure which shelters the second elongated body 104 from direct exposure to, or direct contact with the lumen 110 of the first elongated member 102. As illustrated, the first member or the inner wall 102a defines the lumen 110, in which a biological unit can be encapsulated and preferably retained. The second member 102b defines the outer wall of the removal tool 100. In the embodiment of FIG. 1b, a second elongated body 104 is disposed in a gap or a small annular space 107 formed between the inner wall 102a and the outer wall 102b of the first elongated member 102. As could be detected from FIGS. 1a and 1b, the distal tip 108 of the first elongated body 102 comprises a distal tip of the inner wall 102a and a distal tip of the outer wall 102b. It is blunt and relatively duller that is less sharp) than the sharp distal tip 106 of the second elongated body 104, thus reducing the chance of undesired damage to the tissue to be removed, for example, transecting a follicular unit to be harvested. The distal tip 108 of the first elongated body may be circular, or of any other desired shape. The first elongated body 102 may comprise a taper 112, as seen in FIG. 1a. The taper may be configured in many different ways, for example, by decreasing an overall diameter of the first elongated member at its distal end, or by reducing thickness of the outer wall 102b, or both outer and inner walls 102a and 102b, or by any other means known in the art.

The second elongated body 104 is preferably tubular and it may have the same length or a different length than the first elongated body 102. As seen in the embodiment of FIG. 1b, the second elongated body 104 may be substantially concentrically disposed within the wall structure of the first elongated body 102, such that when a biological unit, such as a follicular unit, enters and moves through the lumen 110 of the first elongated body 102, it is not exposed to or in a potential contact with the sharp distal tip 106 of the second elongated body. The operation of the tool, including various positions of the sharp distal tip of the second elongated body during removal of the biological tissue, is described below in reference to the examples of the embodiments of the method of the invention. The sharp distal tip 106 of the second elongated body 104 includes a sharp or semi-sharp segment primarily for piercing tissue. The second elongated body 104 may further comprise a taper 114 towards the sharp distal tip 106.

Although illustrated as coaxial tubes, one or both of the elongated bodies 102 and 104 may comprise a series of wires, rods or other suitably shaped elements that together form each respective elongated body. The first and second elongated bodies, however formed, may comprise a small annular space between them (for example, an annular space 107 in FIG. 1b), designed such that the tubes rotate slightly off axis to one another, so as to wobble or be mis-aligned with one another. Alternatively, the coaxial tubes may comprise radial spacers (not shown) that maintain the distance between the coaxial elongated members. It will be appreciated by those skilled in the art that the elongated bodies 102 and 104 may be manufactured from the same type or differing materials, from rigid or semi-rigid materials, e.g. stainless steel hypodermic tubing or other appropriate material, such a titanium or nitinol.

One method of use of the removal tool 100 according to an embodiment of the invention is illustrated in FIGS. 2a-2f. In the illustrations, the reader is advised that the focus is on the distal end of the features discussed, and that the proximal end may be configured to suit any particular need. For example, rather than be discrete concentric tubular members, the elongated bodies 102a and 102b may be at least partially attached at the proximal ends thereof. The tool 100 may, for example, be configured to incorporate a handle and/or appropriate sleeves, slidable shafts, or other such structures to move the elongated bodies axially and optionally radially relative to one another. In an alternative embodiment, the proximal end of the tool may adapted to enable one or more of a mechanical system, and electromechanical system, a pneumatic system, hydraulic system or a magnetic system for effecting controlled movement of the first and second elongated bodies relative to one another, and to facilitate a semi- or fully-automated tool to be employed. In yet another alternative embodiment, either or both of the elongated bodies may be operatively coupled to a biasing mechanism, such as a spring mechanism, or other such release mechanism to facilitate movement of the elongated body in the axial direction, in a quick, or slow or otherwise controlled manner.

In one embodiment of the invention, the removal tool can be implemented in a robotically-assisted system, such as those described in the U.S. Publication No. 2007/0106306 already incorporated by reference herein. In this particular embodiment the removal tool 100 may be connected directly or indirectly to an automated (e.g., robotic) arm, so that movement of the removal tool relative to the body surface may be performed by either movement of the robotic arm relative to the body surface, or movement of the removal tool relative to the automated arm, or a combination of each. Operation of the mechanical system, electromechanical system, pneumatic system, hydraulic system or magnetic system, may be controlled by an electronic controller such as a computer of the PC type, an embedded processor, a programmable hardware device, or some other device capable of electronic manipulation and processing of data in accordance with a software and/or another logical control system and/or user input. For example, such programmable hardware devices may include one or more of a field-programmable gate array (FPGA) or application-specific integrated circuit (ASIC).

Figure 2A:
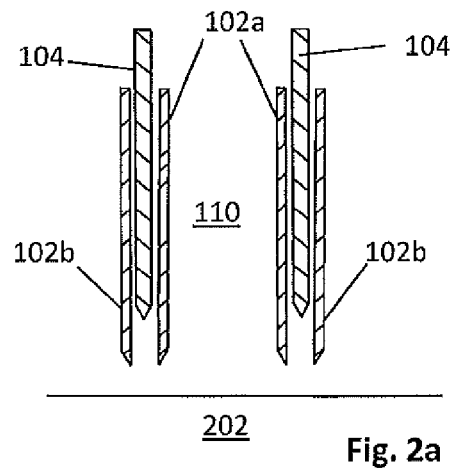
FIGS. 2a-2f show longitudinal sectional views of various stages of operation according to an embodiment of the present invention.

FIGS. 2a-2f illustrate an example of a method by which the removal tool 100 may be operated to remove or harvest a biological unit such as, for example, a hair graft, from a donor area such as a scalp or other body surface containing hair. FIG. 2a illustrates the tool 100 positioned above a body surface 202 and the follicular unit or hair graft (not shown) which is intended to be removed from the donor area. As illustrated, the second elongated body 104 is in its retracted position (e.g., the sharp distal tip of the second elongated body is retracted inside the wall of the first elongated body 102), and the lumen 110 of the tool 100 is clear. In this position, the first member 102a of the first elongated body 102 serves to shield the second elongated body 104 from direct contact or exposure to the lumen 110 of the first elongated body 102. In this position, the sharp distal tip 106 of the removal tool 100 is also protected from contamination or any other such damage from external elements. The user is likewise protected from unintentional puncturing of his/her skin by merely handling the tool 100. The lumen 110, in the context of hair transplantation, may comprise a diameter ranging between 0.5-1.5 mm, and preferably about 1.0 mm, thus making it suitable for receiving follicular units, which are naturally occurring aggregates of 1-3 (and much less commonly, 4-5) closely spaced hair follicles.

Figure 2B:
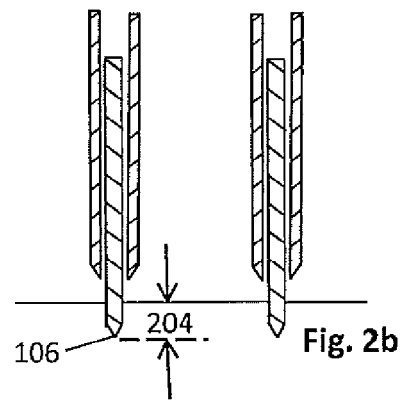

FIG. 2b illustrates the sharp distal tip 106 of the second elongated body 104 having advanced or moved such that the body surface 202 is penetrated, perforated, or cut to a first depth 204. As previously explained, in order to reduce potential damage to the biological tissue, such as a follicular unit, it is preferable to use the sharp distal tip 106 only to pierce the body surface and to create an initial incision. Therefore, it is preferable to keep the first depth 204 to a minimum depth required after which one can successfully continue to dissect tissue with the blunt tip 108 of the first elongated body. For example, such first depth 204 may be approximately 0.5 mm to 2 mm. The movement of the second elongated body may comprise rotational as well as translational motion, and the penetration or perforation may be the result of the sharp distal tip 106 having moved towards the body surface 202 at a relatively high speed.

Figure 2C:
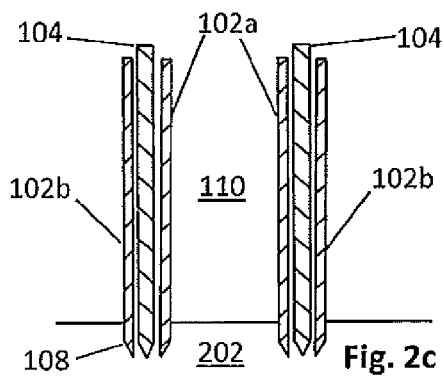
Figure 2D:
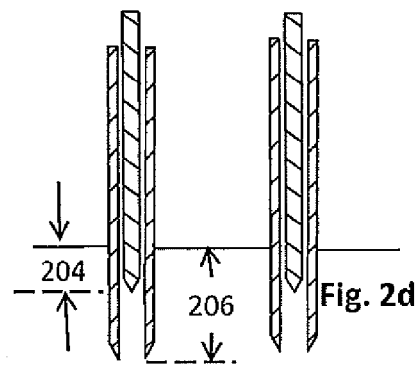

FIG. 2c shows the first elongated body 102 having advanced or moved axially relative to the second elongated body 104, and entering through the body surface 202, for example, through the incision created by the second elongated body 104. Enabling the distal tip 108 of the first elongated body 102 to enter the incision already created by the sharp distal end 106 results in only a single incision or defect on the skin, which is beneficial to the patient. Moreover, by first initiating a path using the sharp distal tip 106 of the second elongated body 104, and subsequently entering the same incision with the blunt distal tip 108 of the first elongated body 102, eliminates the need to recannulate. Since recannulation, including additional realignment of the subsequently inserted elongated body with the follicular unit, is not required, it also saves procedure time and provides an additional benefit for both the system and the patient. The first elongated body 102 continues in its axial (and optionally radial) movement, as illustrated in FIG. 2d, into the cutaneous and subcutaneous tissue to a second depth 206 of, for example, approximately 5-8 mm using the blunt distal end 108 of the first elongated body 102 to dissect or separate the follicular unit from the surrounding tissue. At this second depth 206, the lumen 110 of the first elongated body 102 substantially encapsulates the follicular unit for harvesting. It will be appreciated that the sharp distal tip 106 of the removal tool 100 will more easily pierce the body surface 202 but will be used only until it is inserted to a depth 204. Any further insertion of the tool will be accomplished using the blunt distal end 108 which will have less chance of cutting (transecting) the portion of the hair follicle lying beneath the body surface 202. In particular, as hair follicles often extend at an angle in the cutaneous and subcutaneous tissue region, thus the blunt distal end 108 of the first elongated body may "push" the hair graft and surrounding tissue into the inner lumen 110 without causing transection thereof. During insertion of the first elongated body from the depth 204 until the depth 206, the follicular unit is not exposed to the sharp distal end 106, as the sharp distal end 106 is shielded by the inner wall or the inner member 102a from the lumen 110 of the first elongated body.

Figure 2E:
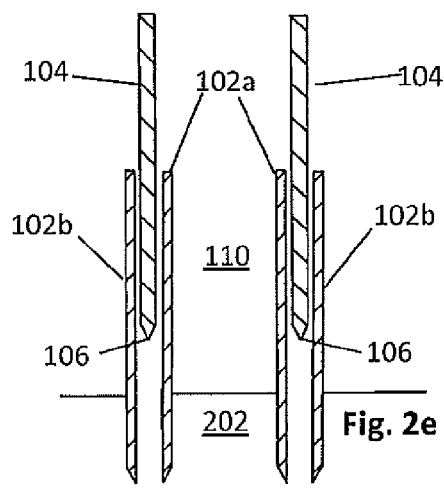
Figure 2F:
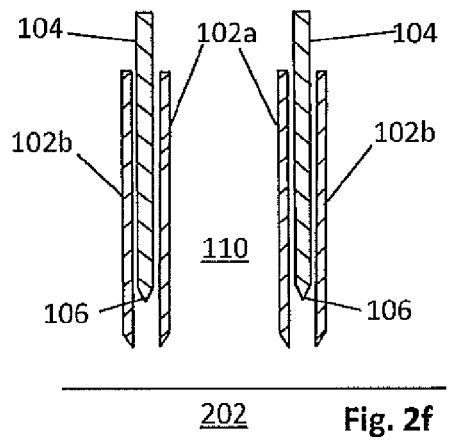

FIGS. 2e and 2f illustrate the withdrawal of the removal tool 100. The second elongated body may be withdrawn before or simultaneously with the withdrawal of the first elongated body. Also, it can be withdrawn with the same or a different speed, as long as the second elongated body 104, including its sharp distal end, is disposed between the members 102a and 102b of the first elongated body 102 during the withdrawal. In other words, the sharp distal tip of the second elongated body is located either proximally or flush with a distal tip of the first elongated body. As illustrated in FIG. 2f, the removal tool 100 is fully withdrawn, preferably with the follicular unit retained within the lumen 110 thereof. It can be seen in FIGS. 2e and 2f, that at no time, throughout the withdrawal of the removal tool from the depth 206 to its location above the body surface 202, is the follicular unit exposed to a surface of the second elongated body 104, and in particular, the follicular unit is not exposed to or in contact with its sharp distal tip 106. In this manner the follicular unit is protected from any edge or surface that could possibly cause it a trauma or stress. The follicular unit can be removed from the body surface intact, with its integrity preserved. Furthermore, as the distally facing tip 106 of the second elongated body 104 is removed from the body surface 202, the user is once again protected from any unintended penetration of his/her skin.

It will be apparent that although the methodology described above as discrete steps, one or more steps may be combined or even deleted, without departing from the intended functionality of the embodiments of the invention. It will also be apparent that the methods described above may be performed manually, or they may be partially or substantially automated, including performed using robotic systems.

It has been described hereinbefore that the removal tool penetrates the body surface 202, causes a biological unit to enter the lumen 110 therein, and then removes the biological unit from the body surface 202. During withdrawal or removal of the tool, however, the biological unit sometimes remains connected in some manner to the tissue that had been surrounding it. For example, a follicular unit may remain attached to the body surface by surrounding connective tissue. Since the surrounding tissue tends to pull back the follicular unit from the removal tool 100, this sometimes results either in tearing the follicular unit apart, or simply not retaining it in the removal tool 100.

There are several ways in which this particular problem can be overcome. One such way is to utilize suction, a pressure differential, within the lumen 110 of the tool 100 to further transfer the follicular unit in a proximal direction. Alternatively, or additionally, retention structures or deformable elements, in the form of barbs, protrusions, grooves, or any other suitably functioning retention element may be utilized to retain the biological unit within the tool 100 as it is retracted from the body surface 202. In some instances, once the biological unit has been received in the lumen 110, the retention member (not shown) can be moved from a retracted to a retention position to retain the biological unit. In other instances, the retention members may be deformable and once the biological unit is in the lumen 110, it is retained therein. Such a retention member may be incorporated into the elongated body 102 or extend into the lumen 110 from outside the elongated body 102. However, in all configurations, the retention member prevents the biological unit from exiting the lumen 110 in the distal direction. In some instances, the retention member may be integrated into the tool itself, as part of, for example the elongated body 102. A "retention member" as used herein refers to a structure, or a mechanism, or a number of structures and/or mechanisms that partially or fully retain biological tissue in a lumen of various removal tools. The retention member may translate into or across the lumen, or radially constrict the lumen in a circumferential manner, for example, simply closing tightly about a follicular unit, located in the lumen to improve its retention and removal without damaging it.

It is often beneficial to irrigate surgical fields, such as during the removal of biological units, such as follicular units. This is a particularly useful function in the context of robotic hair transplantation in which an automated system may be used to harvest multiple follicular units from a body surface. Due to the speed at which such systems work, constant irrigation with, for example, saline will help increase the yield by providing cooling and lubricious fluid at the distal end of the removal tool 100, it will also help to keep the harvested follicular units moist, and reduce dehydration.

The removal tool 100 can be configured to deliver a fluid or a gas, for example, saline or tumescence fluid, by incorporating a fluid/gas conduit that opens, for example, into the concentric space between the first and the second members 102a and 102b respectively. The fluid/gas may be delivered through distal ports or grooves, for example, near the distal tip of the first 102a and/or second 102b members. Additional fluids or gas that may be delivered to the tissue layers, as mentioned above, include but not limited to medications, antibiotics, or healing facilitating solutions.

The foregoing illustrated and described embodiments of the invention are susceptible to various modifications and alternative forms, and it should be understood that the inventions as generally disclosed herein, as well as the specific embodiments described herein, are not limited to the particular forms or methods disclosed, and that many other embodiments are possible within the spirit and the scope of the present inventions. Moreover, although individual features of one embodiment may be discussed herein or shown in the drawings of the one embodiment and not in other embodiments, it should be apparent that individual features of one embodiment may be combined with one or more features of another embodiment or features from a plurality of embodiments. By way of non-limiting example, it will be appreciated by those skilled in the art that particular features or characteristics described in reference to one figure or embodiment may be combined as suitable with features or characteristics described in another figure or embodiment.

It will be further appreciated by those skilled in the art that the invention is not limited to the use of a particular system, and that automated (including robotic), semi-automated, and manual systems and apparatus may be used for positioning and actuating the respective removal tools and other devices and components disclosed herein.

While the invention has been described in its preferred embodiments, it is to be understood that the words which have been used are words of description and not of limitation. Therefore, changes may be made within the appended claims without departing from the true scope of the invention.

What is claimed is:

1. A method of removing follicular units from a body surface, comprising:
    positioning a removal tool adjacent a body surface, the removal tool being configured to encapsulate a follicular unit, and comprising a first elongated tubular body and a second elongated tubular body;
    advancing the second elongated tubular body having a sharp distal tip to penetrate the body surface, wherein advancing the second elongated tubular body comprises axially moving the second elongated tubular body between an inner wall and an outer wall of the first elongated tubular body and extending distally the sharp distal tip of the second elongated tubular body out from between the inner and the outer walls of the first elongated tubular body;
    advancing the first elongated tubular body into the body surface such that a distal tip of the first elongated tubular body extends past the sharp distal tip of the second elongated tubular body to encapsulate the follicular unit within a lumen of the first elongated tubular body; and
    withdrawing the removal tool such that the encapsulated follicular unit is shielded from the sharp distal tip of the second elongated tubular body by the inner wall of the first elongated body.

2. The method of claim 1, wherein the first elongated tubular body comprises a blunt distal tip.

3. The method of claim 1, wherein advancing the first elongated tubular body comprises shielding the follicular unit as it passes into the lumen of the first elongated tubular body from the sharp distal tip of the second elongated tubular body by the inner wall of the first elongated tubular body.

4. The method of claim 1, wherein withdrawing the removal tool comprises keeping the sharp distal tip of the second elongated tubular body between an inner wall and an outer wall of the first elongated tubular body.

5. The method of claim 1, further comprising removing the follicular unit from the body surface with assistance of a retention member.

6. The method of claim 1, further comprising rotating at least one of the first or the second elongated tubular bodies while it is advanced into the body surface.

7. The method of claim 1, further comprising supplying a fluid or gas under pressure to a distal end of the removal tool.

8. The method of claim 1, wherein the method is substantially automated and comprises the use of a robotic arm.

9. The method of claim 1, wherein the first and/or the second elongated tubular body is moved in an axial direction in a slow, quick or otherwise controlled manner by a release mechanism.

10. The method of claim 1, comprising moving the first and/or the second elongated tubular body relative to the other with one or more of a mechanical system, electromechanical system, pneumatic system, hydraulic system or a magnetic system.

11. The method of claim 10, further comprising using a processor for controlling the one or more of a mechanical system, electromechanical system, pneumatic system, hydraulic system or a magnetic system.

12. The method of claim 1, comprising withdrawing the second elongated tubular body before or simultaneously with the withdrawal of the first elongated tubular body.

13. The method of claim 1, comprising withdrawing the first and the second elongated tubular bodies with the same or a different speed.

14. The method of claim 6, wherein rotating of the at last one of the first or the second elongated tubular bodies comprises rotating slightly off axis to one another.

* * * * *